United States Patent
Sadat-Aalaee et al.

(10) Patent No.: US 6,864,234 B1
(45) Date of Patent: Mar. 8, 2005

(54) SOMATOSTATIN AGONISTS

(75) Inventors: Dean Sadat-Aalaee, La Jolla, CA (US); Barry A. Morgan, Franklin, MA (US)

(73) Assignee: Societe de Conseils de Recherches et d'Applications Scientifiques, S.A.S., Paris (FR)

( * ) Notice: Subject to any disclaimer, the term of this patent is extended or adjusted under 35 U.S.C. 154(b) by 0 days.

(21) Appl. No.: 09/980,943

(22) PCT Filed: Jun. 23, 2000

(86) PCT No.: PCT/US00/17401

§ 371 (c)(1),
(2), (4) Date: Feb. 22, 2002

(87) PCT Pub. No.: WO01/00676

PCT Pub. Date: Jan. 4, 2001

Related U.S. Application Data

(60) Provisional application No. 60/141,028, filed on Jun. 25, 1999.

(51) Int. Cl.$^7$ .................... A61K 38/31; C07K 14/655
(52) U.S. Cl. ........................ 514/11; 530/311
(58) Field of Search ................ 435/7.21; 424/1.69, 424/9.44; 514/11, 15, 16; 530/311

(56) References Cited

U.S. PATENT DOCUMENTS

| 4,603,120 A | 7/1986 | Kamber ............ 514/11 |
| 5,705,483 A | 1/1998 | Galloway et al. ...... 517/12 |

FOREIGN PATENT DOCUMENTS

| EP | 0 505 680 A1 | 9/1992 |
| HU | P9802372 A | 3/1999 |
| WO | WO 95/04752 | 2/1995 |
| WO | WO 98/24807 | 6/1998 |
| WO | WO 98/50063 | 11/1998 |
| WO | WO 98/51330 | 11/1998 |
| WO | WO 98/51331 | 11/1998 |
| WO | WO 98/51332 | 11/1998 |

OTHER PUBLICATIONS

Stenesh. Dictionary of Biochemistry And Molecular Biology, Second Edition. New York: John Wiley & Sons. 1989, p. 347.*

Coy, D.H. et al., "Somatostatin Receptor Antagonists Based on a Mixed Neuromedin B Antagonist/Somatostatin Agonist", Proceedings of the American Peptide Symposium, pp. 526–529, (1999) XP000917964.

Hocart, S.J. et al., "Potent Antagonists of Somatostatin: Synthesis and Biology", Journal of Medicinal Chemistry, vol. 41, No. 7, pp. 1146–1154, (1998) XP000749590.

Raynor, K. et al., "Characterization of Cloned Somatostatin Receptors SSTR4 and SSTR5" Molecular Pharmacology, vol. 44, No. 2, pp. 385–392, (1993).

* cited by examiner

*Primary Examiner*—Jeffrey Edwin Russel
(74) *Attorney, Agent, or Firm*—Fish & Richardson; Brian R. Morrill; Alan F. Feeney

(57) ABSTRACT

The present invention is directed to cyclic peptides of formula (I): $X-A^1-cyclo(D-Cys-A^3-A^4-Lys-A^6-A^7)-A^8-Y$, or a pharmaceutically acceptable salt thereof. The peptides bind selectively to the somatostatin subtype receptor type-5 and elicit an agonist effect from the somatostatin subtype receptors. The peptides are useful for treating a variety of diseases, including Cushings Syndrome, gonadotropinoma, hyperparathyroidism, Paget's disease, VIPoma, nesidioblastosis, hyperinsulinism, gastrinoma, Zollinger-Ellison Syndrome, hypersecretory diarrhea related to AIDS and other conditions, irritable bowel syndrome, pancreatitis, Crohn's Disease, systemic sclerosis, thyroid cancer, psoriasis, hypotension, panic attacks, sclerodoma, small bowel obstruction, gastroesophageal reflux, duodenogastric reflux, Graves' Disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, inhibiting the accelerated growth of a solid tumor, decreasing body weight, treating insulin resistance, Syndrome X, prolonging the survival of pancreatic cells, fibrosis, hyperlipidemia, hyperamylinemia, hyperprolactinemia and prolactinemia.

6 Claims, No Drawings

SOMATOSTATIN AGONISTS

CROSS REFERENCE TO RELATED APPLICATIONS

This application is a U.S. national filing under 35 U.S.C. §371 of international (PCT) application No. PCT/US00/17401, filed Jun. 23, 2000, designating the U.S., and claiming priority to U.S. provisional application Ser. No. 60/141,028, filed Jun. 25, 1999.

BACKGROUND OF THE INVENTION

The present invention is directed to cyclic peptides that have somatostatin agonist activity, as defined by formula (I), shown and defined hereinbelow, or a pharmaceutically acceptable salt thereof, pharmaceutical compositions comprising said peptides and the use thereof as a somatostatin receptor subtypes agonist. The peptides of the present invention bind selectively to the somatostatin subtype receptor 5 and elicit an agonist effect from the somatostatin subtype receptors that the peptides bind to.

Somatostatin (SRIF) is a cyclic tetradecapeptide hormone containing a disulfide bridge between position 3 and position 14 (Heiman, et al., Neuroendocrinology, 45:429–436 (1987)) and has the properties of inhibiting the release of growth hormone (GH) and thyroid-stimulating hormone (TSH), inhibiting the release of amylin, insulin and glucagon, reducing gastric secretion and neurotransmitter release. Metabolism of somatostatin by aminopeptidases and carboxypeptidases leads to a short duration of action. Because of the short half-life of the native somatostatin, various somatostatin analogs have been developed, e.g., for the treatment of acromegaly. Raynor, et al., Molecular Pharmacol. 43:838 (1993).

Five distinct somatostatin receptors have been identified and characterized. Hoyer, et al., Naunyn-Schmiedeberg's Arch. Pharmacol., 350:441 (1994). Somatostatin binds to five distinct receptor (SSTR) subtypes with relatively high and equal affinity for each subtype. Binding to the different types of somatostatin subtypes have been associated with the treatment of the following conditions and/or diseases. ("SSTR-2") (Raynor, et al., Molecular Pharmacol. 43:838 (1993); Lloyd, et al., Am. J. Physiol. 26B:G102 (1995)) while the inhibition of insulin has been attributed to the somatostatin type-5 receptor ("SSTR-5") (Coy, et al. 197:366–371 (1993)). Activation of types 2 and 5 have been associated with growth hormone suppression and more particularly GH secreting adenomas (Acromegaly) and TSH secreting adenomas. Activation of type 2 but not type 5 has been associated with treating prolactin secreting adenomas. Other indications associated with activation of the somatostatin subtypes are inhibition of insulin and/or glucagon and more particularly diabetes mellitus, angiopathy, proliferative retinopathy, dawn phenomenon and Nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; retinopathy; chronic allograft rejection; angioplasty; preventing graft vessel and gastrointestinal bleeding. It is preferred to have an analog which is selective for the specific somatostatin receptor subtype responsible for the desired biological response, thus, reducing interaction with other receptor subtypes which could lead to undesirable side effects.

The peptides of formula (I) are a sub-genus encompassed by a genus of compounds described and claimed in U.S. application Ser. No. 08/855,204, filed May 13, 1997, now U.S. Pat. No. 6,262,229, issued Jul. 17, 2001 and assigned in part to the assignee of the present invention. The compounds of formula (I) of the present application are not specifically described in U.S. Pat. No. 6,262,229. It has been unexpectedly and surprisingly discovered that the compounds of formula (I) of the present invention possess somatostatin agonist activity. This is an unexpected and surprising discovery since the compounds of U.S. Pat. No. 6,262,229 were originally found to possess somatostatin antagonist activity.

SUMMARY OF THE INVENTION

In one aspect, the present invention is directed to a peptide of the formula (I), $$X\text{-}A^1\text{-cyclo}(D\text{-Cys-}A^3\text{-}A^4\text{-Lys-}A^6\text{-}A^7)\text{-}A^8\text{-}Y. \quad (I)$$

or a pharmaceutically acceptable salt thereof, wherein

X is H,  or

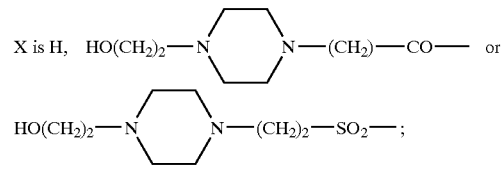

$A^1$ and $A^3$ are each independently the D- or L-isomer of an amino acid selected from the group consisting of Phe, Tyr, Tyr(I), Trp, 3-Pal, 4-Pal, Cpa and Nal;
$A^4$ is L-Trp, D-Trp, L-β-methyl-Trp or D-β-methyl-Trp;
$A^6$ is —NH—(CHR$^1$)$_n$—CO—, where n is 2, 3, or 4;
$A^7$ is L- or D-Cys;
$A^8$ is the D- or L-isomer of an amino acid selected from the group consisting of Phe, Tyr, Tyr(I), Trp, Nal, Cpa, Val, Leu, Ile, Ser and Thr;
Y is NR$^2$R$^3$ where R$^2$ and R$^3$ are each independently H or (C$_1$–C$_5$)alkyl;
R$^1$ is selected from the group consisting H, (C$_1$–C$_4$)alkyl and —CH$_2$-aryl; wherein said aryl is an optionally substituted moiety selected from the group consisting of phenyl, 1-naphthyl, and 2-naphthyl, wherein said optionally substituted moiety is optionally substituted with one or more substituents each independently selected from the group consisting of (C$_{1-6}$)alkyl, (C$_{2-6}$)alkenyl, (C$_{2-6}$)alkynyl, aryl, aryl(C$_{1-6}$)alkyl, (C$_{1-6}$)alkoxy, —N(R$^4$R$^5$), —COOH, —CON(R$^4$R$^5$), halo, —OH, —CN, and —NO$_2$;
R$^4$ and R$^5$ each is, independently for each occurrence, H or (C$_{1-3}$)alkyl;
where the Cys of A$^2$ is bonded to the Cys of A$^7$ by a di-sulfide bond formed from the thiol groups of each Cys.

A preferred group of peptides of the foregoing peptide of formula (I) is wherein
X is H;
A$^1$ is L-Phe, D-Phe, L-Cpa or D-Cpa;
A$^3$ is L-Tyr, L-Trp or L-3-Pal;
A$^4$ is D-Trp;
A$^6$ is β-Ala or Gaba;
A$^7$ is L-Cys;
A$^8$ is Thr, L-Trp, L-Leu or L-Nal; and
R$^2$ and R$^3$ are each H; or a pharmaceutically acceptable salt thereof.

Preferred peptides of the immediately foregoing group of peptides are:

Cpa-cyclo(D-Cys-3-Pal-D-Trp-Lys-Gaba-Cys)-Nal-NH$_2$;
Cpa-cyclo(D-Cys-3-Pal-D-Trp-Lys-β-Ala-Cys)-Nal-NH$_2$;
Phe-cyclo(D-Cys-3-Pal-D-Trp-Lys-Gaba-Cys)-Nal-NH$_2$;
Phe-cyclo(D-Cys-Tyr-D-Trp-Lys-Gaba-Cys)-Nal-NH$_2$;
Phe-cyclo(D-Cys-Trp-D-Trp-Lys-Gaba-Cys)-Nal-NH$_2$;
Phe-cyclo(D-Cys-Tyr-D-Trp-Lys-Gaba-Cys)-Trp-NH$_2$;
D-Phe-cyclo(D-Cys-Tyr-D-Trp-Lys-Gaba-Cys)-Nal-NH$_2$;
D-Phe-cyclo(D-Cys-Tyr-D-Trp-Lys-Gaba-Cys)-Leu-NH$_2$; and
Phe-cyclo-(D-Cys-Tyr-D-Trp-Lys-Gaba-Cys)-Thr-NH$_2$; or a pharmaceutically acceptable salt thereof.

Preferred peptides of the immediately foregoing group of peptides are:
Cpa-cyclo(D-Cys-3-Pal-D-Trp-Lys-Gaba-Cys)-Nal-NH$_2$; and
Cpa-cyclo(D-Cys-3-Pal-D-Trp-Lys-β-Ala-Cys)-Nal-NH$_2$; or a pharmaceutically acceptable salt thereof.

In another aspect, the present invention provides a pharmaceutical composition useful for eliciting a somatostatin agonist response in a human or other animal which comprises an effective amount of a peptide of formula (I) or a pharmaceutically acceptable salt thereof, and a pharmaceutically acceptable carrier.

In yet another aspect, the present invention provides a method of eliciting a somatostatin agonist response in a human or other animal in need thereof, which comprises administering an effective amount of a peptide of formula (I) or a pharmaceutically acceptable salt thereof to the human or other animal.

In a further aspect, the present invention provides a method of selectively binding a somatostatin subtype receptor type 5 in a human or other animal, which comprises administering an effective amount of a peptide of formula (I) or a pharmaceutically acceptable salt thereof to the human or other animal.

In still a further aspect, the present invention provides a method of treating a disease or condition in a human or other animal in need thereof, which comprises administering an effective amount of a peptide of formula (I) or a pharmaceutically acceptable salt thereof to the human or other animal, wherein said disease or condition is selected from the group consisting of Cushings Syndrome, gonadotropinoma, hyperparathyroidism, Paget's disease, VIPoma, nesidioblastosis, hyperinsulinism, gastrinoma, Zollinger-Ellison Syndrome, hypersecretory diarrhea related to AIDS and other conditions, irritable bowel syndrome, pancreatitis, Crohn's Disease, systemic sclerosis, thyroid cancer, psoriasis, hypotension, panic attacks, sclerodoma, small bowel obstruction, gastroesophageal reflux, duodenogastric reflux, Graves' Disease, polycystic ovary disease, upper gastrointestinal bleeding, pancreatic pseudocysts, pancreatic ascites, leukemia, meningioma, cancer cachexia, acromegaly, restenosis, hepatoma, lung cancer, melanoma, inhibiting the accelerated growth of a solid tumor, decreasing body weight, treating insulin resistance, Syndrome X, prolonging the survival of pancreatic cells, fibrosis, hyperlipidemia, hyperamylinemia, hyperprolactinemia and prolactinemia.

In still a further aspect, the present invention provides a method of inhibiting the secretion of growth hormone, insulin, glucagon or pancreatic exocrine secretion in a human or other animal in need thereof, which comprises administering a peptide of formula (I) or a pharmaceutically acceptable salt thereof to said human or other animal.

In an even further aspect, the present invention provides a method of imaging cells containing somatostatin receptors in vivo in a human or other animal, which comprises administering a peptide of formula (I), provided that at least one of A$^1$, A$^3$ or A$^8$ is Tyr(I), or a pharmaceutically acceptable salt thereof to said human or other animal.

In another aspect, the present invention provides a method of imaging cells containing somatostatin receptors in vitro, which comprises administering a peptide of formula (I), provided that at least one of A$^1$, A$^3$ or A$^8$ is Tyr(I), or a pharmaceutically acceptable salt thereof to said human or other animal. Such peptides of the present invention can be used either in vivo to detect cells having somatostatin receptors (e.g., cancer cells) or in vitro as a radioligand in a somatostatin receptor binding assay.

The three letter abbreviations accepted in the art are used to refer to the amino acids in a peptide of the present invention. In the formula set forth herein, the disulfide bond between the thiol group on the side chain of residue A$_2$ (i.e., D-Cys) and the thiol group on the side chain of residue A$_7$ (i.e., L-Cys or D-Cys) is not shown. The following amino acid abbreviations stand for the name indicated next to it: Cpa=p-chlorophenylalanine; Nal=β-(2-naphthyl)alanine; 3-Pal=β-(3-pyridyl)-alanine; 4-Pal=β-(4-pyridyl)-alanine; and Gaba=4-aminobutyric acid. The definition of "—NH—(CH$_2$)$_n$—CO— where n is 2, 3, or 4" encompasses such amino acids as β-Ala and Gaba.

Unless noted otherwise, the three letter abbreviation of an amino acid refers to the L-isomer.

The term alkyl is intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, and the like. When the term C$_0$-alkyl is included in a definition it is intended to denote a single covalent bond.

The term alkenyl is intended to include hydrocarbon groups having one or more double bonds and the designated number of carbon atoms in either a straight or branched configuration. Exemplary of such alkenyl groups are ethenyl, propenyl, isopropenyl, butenyl, sec-butenyl, tertiary butenyl, pentenyl, isopentenyl, hexenyl, isohexenyl and the like.

The term alkynyl is intended to include those alkynyl groups, i.e., hydrocarbon groups having one or more triple bonds, having the designated number of carbon atoms in either a straight or branched configuration. Exemplary of such alkynyl groups are ethynyl, propynyl, butynyl, pentynyl, isopentynyl, hexynyl, isohexynyl and the like.

The term alkoxy is intended to include those alkoxy groups having the designated number of carbon atoms in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term aryl is intended to include aromatic rings known in the art, which can be mono-cyclic or bi-cylic, such as phenyl and naphthyl.

The term halo is intended to include chlorine, bromine, iodine, and fluorine.

DETAILED DESCRIPTION

One skilled in the art can, based on the description herein, utilize the present invention to its fullest extent. The following specific embodiments are, therefore, to be construed as merely illustrations of the invention and is not meant to be construed as limiting the full scope of the invention.

Peptides of the present invention can be and were synthesized on Rink Amide MBHA resin, (4-(2',4'-dimethoxyphenyl-Fmoc-aminomethyl)-phenoxyacetamidonorleucyl-MBHA resin), using a standard solid phase protocol for FMOC chemistry and cleaved from the resin with a TFA/Phenol/H$_2$O/triisopropylsilane (83 ml/5 g/10 ml/2 ml) mixture. Peptides were cyclized in CH$_3$CN/H$_2$O (5 ml/5 ml) using EKATHIOX™ resin (EKAGEN Corporation, San Carlos, Calif.) and purified on C$_{18}$ silica (Rainin Instruments Co., Woburn, Mass. now Varian Analytical, Walnut Creek, Calif.), using acetonitrile/0.1% trifluoroacetic acid buffers. Homogeneity was assessed by analytical HPLC and were determined to be >95% for each peptide. Peptides were characterized by mass spectrometry.

The synthesis of iodinated Tyr (Tyr(I)) peptides of formula (I) of the present invention (e.g., the chloramine-T method) is well documented and are within the ability of a person of ordinary skill in the art. See, e.g., Czernick, et al., J. Biol. Chem. 258:5525 (1993) and European Patent No. 389,180 B1.

A peptide of formula (I) wherein X is

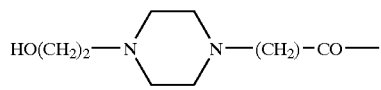

or

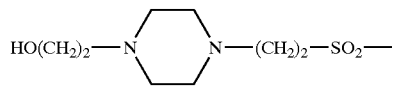

can be synthesized according to the processes and teachings of U.S. Pat. No. 5,552,520, the contents of which are incorporated herein in its entirety.

Below is a detailed description of the synthesis of Examples 1 and 2. Other peptides within a compound of formula (I) can be prepared by making appropriate modifications, well-known to one of ordinary skill in the art of peptide synthesis.

EXAMPLE 1

Step 1=Preparation of Fmoc-Cpa-S-trityl-D-Cys-Pal-N-in-t-Boc-D-Trp-N-ε-t-Boc-Lys-β-Ala-S-trityl-Cys-Nal-4-(2',4'-Dimethoxyphenylamino methyl) phenoxy-acetamido-norleucyl-4-methylbenzhydrylamine resin.

Rink amide MBHA resin (Novabiochem, Inc., San Diego, Calif.) 0.5 g, (0.265 mmole), was placed in a reaction vessel of a 24-RV peptide synthesizer, assembled by connecting a shaker (from the Burrell Wrist-Action Laboratory Shaker), a solvent distributor and a vacuum pump. The peptide synthesizer was programmed to perform the following reaction cycle:
  a. Dimethylformamide;
  b. 25% piperidine in dimethylformamide (manually added) (2 times for 15 minutes each with 1 time wash with DMF in between);
  c. DMF washes (3×10 mL, 1 minute each);
The resin was stirred with FMOC-Nal (1.06 mmol), 2-(1H-benzotriazol-1-yl)-1,1,3,3-tetramethyluronium hexafluorophosphate (HBUT) 1.007 mmole), and diisopropylethyl amine (2.12 mmole) in dimethylformamide for about 1½ hours and the resulting amino acid resin was then cycled through steps (a) to (c) in the above washing/deblocking program.

The following amino acids were coupled successively to the Nal-resin by the same procedure: Fmoc-S-Trityl-Cys, Fmoc-β-Ala, N-ε-t-Boc-Lys, Fmoc-(N-in-t-Boc)-D-Trp, Fmoc-Pal, Fmoc-S-trityl-D-Cys, and Fmoc-p-Cl-Phe.

After washing with DMF (3×10 mL, about 1 minute each) and drying under vacuum, the complete peptide resin weighed 0.749 g.

Step 2: Preparation of H-Cpa-cyclo(D-Cys-Pal-D-Trp-Lys-β-Ala-Cys)-Nal-NH$_2$

The peptide resin obtained from Step 1 of Example 1 (0.36 g, 0.087 mmole) was mixed with a freshly prepared solution of TFA (8.8 mL), phenol (0.5 g), H$_2$O (0.5 mL) and triisopropylsilane (0.2 mL) at room temperature and stirred for about 2½ hours. Excess TFA was evaporated under reduced pressure to yield an oily residue. Ether was then added to the oily residue and the free linear peptide was precipitated, filtered, and washed with dry ether. The crude peptide was then dissolved in 10 mL of CH$_3$CN/H$_2$O (5 mL/5 mL), followed by the addition of 200 mg EKATHIOX™ resin. The mixture was stirred overnight and filtered. The filtrate was evaporated to a small volume then applied to a column (22–250 mm) of microsorb octadecyl-silane silica (5 μm). Elution with a linear gradient (20% to 40%, over 60 minutes) of acetonitrile in water, (both solvents have 0.1% trifluoroacetic acid) yields fractions which were examined by analytical high performance liquid chromatography ("HPLC") and pooled to give maximum purity. Lyophilization of the solution from water gave 26 mg of the product as white, fluffy powder. The product was found to be homogeneous by HPLC C$_{18}$ silica using the same eluant as described above and a linear gradient (30% to 70%, over 15 min) (Retention Time—6.313 minutes). Infusion mass spectrometry confirmed the composition of the cyclic octapeptide, MW 1133.8.

EXAMPLE 2

Step 1: Preparation of Fmoc-Cpa-S-trityl-D-Cys-Pal-in-t-Boc-D-Trp-N-ε-t-Boc-Lys-Gaba-S-trityl-Cys-Nal-4-(2',4'-Dimethoxyphenylaminomethyl) Phenoxyacetamido-norleucyl-4-methylbenzhydrylamine resin Rink amide MBHA resin (Novabiochem, Inc. San Diego, Calif.) 0.2 g, (0.106 mmole) was placed in reaction vessel #3, (RV-3) of the 24-RV peptide synthesizer. The peptide synthesizer was programmed to perform the following reaction cycle:
  a. Dimethylformamide;
  b. 25% piperidine in dimethylformamide (manually added) (2 times for 15 minutes each with 1 time wash with DMF in between);
  c. DMF washes (3×10 mL, 1 minute each);
The resin was stirred with FMOC-Nal (0.424 mmol), 2-(1H-benzotriazol-1-yl)-1,1,3,3-tetramethyluronium hexafluorophosphate (HBUT) 0.403 mmole), and diisopropylethyl amino (0.848 mmole) in dimethylformamide for about 1½ hours and the resulting amino acid resin was then cycled through steps (a) to (c) in the above wash program.

The following amino acids were coupled successively to the peptide resin by the same procedure: Fmoc-S-Trityl-Cys, Fmoc-Gaba, N-ε-t-Boc-Lys, Fmoc-N-in-t-Boc)-D-Trp, Fmoc-Pal, Fmoc-S-trityl-D-Cys, and Fmoc-Cpa. After washing with DMF (3×10 mL, about 1 minute each) and drying under vacuum, the complete resin weighed 0.31 g.

Step 2: Preparation of H-Cpa-cyclo(D-Cys-Pal-D-Trp-Lys-Gaba-Cys)-Nal-NH$_2$

The peptide resin obtained from Step 1 of Example 2 was mixed with a freshly prepared solution of TFA (8.3 mL), phenol (0.5 g), H$_2$O (1 mL) and triisopropylsilane (0.2 mL) at room temperature and stirred for about 2½ hours. Excess TFA was evaporated under reduced pressure to give an oily residue. Ether was then added to the oily residue and the free linear peptide was precipitated, filtered, and then washed with dry ether. The crude peptide was then dissolved in 10 mL of $CH_3CN/H_2O$ followed by the addition of 200 mg of EKATHIOX™ resin. The mixture was stirred overnight and filtered. The filtrate was evaporated to a small volume then applied to a column (22–250 mm) of microsorb octadecyl-silane silica (5 µm), and eluted with a linear gradient (20% to 100%, over 60 minutes) of acetonitrile in water, in which both solvents have 0.1% trifluoroacetic acid. Fractions were examined by analytical high performance liquid chromatography ("HPLC") and pooled to give maximum purity. Lyophilization of the solutions from water gave 13 mg of the product as white, fluffy powder. The product was found to be homogeneous by HPLC $C_{18}$ silica using the same eluant as described above (20% to 80%, over 15 min) (Retention time—9.195 minutes). Infusion mass spectrometry confirmed the composition of the cyclic octapeptide, MW 1147.83.

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt by dissolving the peptide in a small amount of 0.25 N acetic acid aqueous solution. The resulting solution is applied to a semi-prep HPLC column (Zorbax, 300 SB, C-8). The column is eluted with (1) 0.1N ammonium acetate aqueous solution for 0.5 hrs., (2) 0.25N acetic acid aqueous solution for 0.5 hrs. and (3) a linear gradient (20% to 100% of solution B over 30 min.) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

The affinity of a peptide of the present invention for human somatostatin subtype receptors 1 to 5 ($sst_1$, $sst_2$, $sst_3$, $sst_4$ and $sst_5$, respectively) is determined by measuring the inhibition of ($^{125}$I-Tyr$^{11}$)SRIF-14 binding to CHO-K1 transfected cells.

The human $sst_1$ receptor gene was cloned as a genomic fragment. A 1.5 Kb PstI-XmnI segment containing 100 bp of the 5'-untranslated region, 1.17 Kb of the entire coding region, and 230 bp of the 3'-untranslated region was modified by the BglII linker addition. The resulting DNA fragment was subcloned into the BamHI site of a pCMV-81 to produce the mammalian expression plasmid (provided by Dr. Graeme Bell, Univ. Chicago). A clonal cell line stably expressing the $sst_1$ receptor was obtained by transfection into CHO-K1 cells (ATCC) using the calcium phosphate co-precipitation method (1). The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_2$ somatostatin receptor gene, isolated as a 1.7 Kb BamHI-HindIII genomic DNA fragment and subcloned into the plasmid vector pGEM3Z (Promega), was kindly provided by Dr. G. Bell (Univ. of Chicago). The mammalian cell expression vector is constructed by inserting the 1.7 Kb BamH1-HindII fragment into compatible restriction endonuclease sites in the plasmid pCMV5. A clonal cell line is obtained by transfection into CHO-K1 cells using the calcium phosphate co-precipitation method. The plasmid pRSV-neo is included as a selectable marker.

The human $sst_3$ was isolated at genomic fragment, and the complete coding sequence was contained within a 2.4 Kb BamHI/HindIII fragment. The mammalian expression plasmid, pCMV-h3 was constructed by inserting the a 2.0 Kb NcoI-HindIII fragment into the EcoR1 site of the pCMV vector after modification of the ends and addition of EcoR1 linkers. A clonal cell line stably expressing the $sst_3$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human sst receptor expression plasmid, pCMV-HX was provided by Dr. Graeme Bell (Univ. Chicago). The vector contains the 1.4 Kb NheI-NheI genomic fragment encoding the human $sst_4$, 456 bp of the 5'-untranslated region and 200 bp of the 3'-untranslated region, clone into the XbaI/EcoR1 sites of PCMV-HX. A clonal cell line stably expressing the $sst_4$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_5$ gene was obtained by PCR using a λ genomic clone as a template, and kindly provided by Dr. Graeme Bell (Univ. Chicago). The resulting 1.2 Kb PCR fragment contained 21 base pairs of the 5'-untranslated region, the full coding region, and 55 bp of the 3'-untranslated region. The clone was inserted into EcoR1 site of the plasmid pBSSK(+). The insert was recovered as a 1.2 Kb HindIII-XbaI fragment for subcloning into pCVM5 mammalian expression vector. A clonal cell line stably expressing the $SST_5$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

CHO-K1 cells stably expressing one of the human sst receptor are grown in RPMI 1640 containing 10% fetal calf serum and 0.4 mg/ml geneticin. Cells are collected with 0.5 mM EDTA, and centrifuged at 500 g for about 5 min. at about 4° C. The pellet is resuspended in 50 mM Tris, pH 7.4 and centrifuged twice at 500 g for about 5 min. at about 4° C. The cells are lysed by sonication and centrifuged at 39000 g for about 10 min. at about 4° C. The pellet is resuspended in the same buffer and centrifuged at 50000 g for about 10 min. at about 4° C. and membranes in resulting pellet are stored at −80° C.

Competitive inhibition experiments of ($^{125}$I-Tyr$^{11}$)SRIF-14 binding are run in duplicate in polypropylene 96 well plates. Cell membranes (10 µg protein/well) are incubated with ($^{125}$I-Tyr$^{11}$)SRIF-14 (0.05 nM) for about 60 min. at about 37° C. in 50 mM HEPES (pH 7.4), 0.2% BSA, 5 mM $MgCl_2$, 200 KIU/ml Trasylol, 0.02 mg/ml bacitracin and 0.02 mg/ml phenylmethylsulphonyl fluoride.

Bound from free ($^{125}$I-Tyr$^{11}$)SRIF-14 is separated by immediate filtration through GF/C glass fiber filter plate (Unifilter, Packard) presoaked with 0.1% polyethylenimine (P.E.I.), using Filtermate 196 (Packard) cell harvester. Filters are washed with 50 mM HEPES at about 0–4° C. for about 4 sec. and assayed for radioactivity using Packard Top Count.

Specific binding is obtained by subtracting nonspecific binding (determined in the presence of 0.1 μM SRIF-14) from total binding. Binding data are analyzed by computer-assisted nonlinear regression analysis (MDL) and inhibition constant (Ki) values are determined.

The determination of whether a compound of the instant invention is an agonist or an antagonist is determined by the following assay.

Functional assay: Inhibition of CAMP intracellular production:

CHO-K1 Cells expressing human somatostatin (SRIF-14) subtype receptors are seeded in 24-well tissue culture multidishes in RPMI 1640 media with 10% FCS and 0.4 mg/ml geneticin. The medium is changed the day before the experiment.

Cells at $10^5$ cells/well are washed 2 times by 0.5 ml and fresh RPMI with 0.2% BSA supplemented with 0.5 mM (1) 3-isobutyl-1-methylxanthine (IBMX) and incubated for about 5 min at about 37° C.

Cyclic AMP production is stimulated by the addition of 1 mM forskolin (FSK) for about 15–30 minutes at about 37° C.

The agonist effect of a compound is measured by the simultaneous addition of FSK (1 μM), SRIF-14 ($10^{-12}$ M to $10^{-6}$ M) and a test compound ($10^{-10}$ M to $10^{-5}$ M).

The antagonist effect of a compound is measured by the simultaneous addition of FSK (1 μM), SRIF-14 (1 to 10 nM) and a test compound ($10^{-10}$ M to $10^{-5}$ M).

The reaction medium is removed and 200 ml 0.1 N HCl is added. CAMP is measured using radioimmunoassay method (Kit FlashPlate SMP001A, New England Nuclear).

As is well known to those skilled in the art, the known and potential uses of somatostatin are varied and multitudinous. Thus, the administration of a peptide of this invention for purposes of stimulating the somatostatin receptors can have the same effects or uses as somatostatin itself. For example, inhibiting the secretion of growth hormone, insulin, glucagon and pancreatic exocrine secretion (U.S. Pat. No. 4,853, 371); for treating restenosis (U.S. Pat. No. 5,147,856); for treating hepatoma (U.S. Pat. No. 5,411,943); for treating lung cancer (U.S. Pat. No. 5,073,541); treating melanoma (U.S. Pat. No. 6,087,337 issued Jul. 11, 2000; for inhibiting the accelerated growth of a solid tumor (U.S. Pat. No. 5,504,069); for decreasing body weight (WO 98/51331 published Nov. 19, 1998); for treating insulin resistance and Syndrome X (WO 98/51332 published Nov. 19, 1998); for prolonging the survival of pancreatic cells (U.S. Pat. No. 5,688,418); for treating fibrosis (WO 98/08529 published Mar. 5, 1998); for treating hyperlipidemia (WO 98/51330 published Nov. 19, 1998); for treating hyperamylinemia (U.S. Pat. No. 5,763,200 issued Jun. 9, 1998); for treating hyperprolactinemia and prolactinomas (U.S. Pat. No. 5,972, 893 issued Oct. 26, 1999); Cushings Syndrome (see Clark, R. V. et al, Clin. Res. 38, p. 943A, 1990); gonadotropinoma (see Ambrosi B., et al., Acta Endocr. (Copenh.) 122, 569–576, 1990); hyperparathyroidism (see Miller, D., et al., Canad. Med. Ass. J., Vol. 145, pp. 227–228, 1991); Paget's disease (see, Palmieri, G. M. A., et al., J. of Bone and Mineral Research, 7, (Suppl. 1), p. S240 (Abs. 591), 1992); VIPoma (see Koberstein, B., et al., Z. Gastroenterology, 28, 295–301, 1990 and Christensen, C., Acta Chir. Scand. 155, 541–543, 1989); nesidioblastosis and hyperinsulinism (see Laron, Z., Israel J. Med. Sci., 26, No. 1, 1–2, 1990, Wilson, D. C., Irish J. Med. Sci., 158, No. 1, 31–32, 1989 and Micic, D., et al., Digestion, 16, Suppl. 1.70. Abs. 193, 1990); gastrinoma (see Bauer, F. E., et al., Europ. J. Pharmacol., 183, 55 1990); Zollinger-Ellison Syndrome (see Mozell, E., et al., Surg. Gynec. Obstet., 170, 476–484, 1990); hypersecretory diarrhea related to AIDS and other conditions (due to AIDS, see Cello, J. P., et al., Gastroenterology, 98, No. 5, Part 2, Suppl., A163 1990; due to elevated gastrin-releasing peptide, see Alhindawi, R., et al., Can. J. Surg., 33, 139–142, 1990; secondary to intestinal graft vs. host disease, see Bianco J. A., et al., Transplantation, 49, 1194–1195, 1990; diarrhea associated with chemotherapy, see Petrelli, N., et al., Proc. Amer. Soc. Clin. Oncol., Vol. 10, P 138, Abstr. No. 417 1991); irritable bowel syndrome (see O'Donnell, L. J. D., et al., Aliment. Pharmacol. Therap., Vol. 4., 177–181, 1990); pancreatitis (see Tulassay, Z., et al., Gastroenterology, 98, No. 5, Part 2, Suppl., A238, 1990); Crohn's Disease (see Fedorak, R. N., et al., Can. J. Gastroenterology, 3, No.2, 53–57, 1989); systemic sclerosis (see Soudah, H., et al., Gastroenterology, 98, No. 5, Part 2, Suppl., A129, 1990); thyroid cancer (see Modigliani, E., et al., Ann., Endocr. (Paris), 50, 483–488, 1989); psoriasis (see Camisa, C., et al., Cleveland Clinic J. Med., 57, No. 1, 71–76, 1990); hypotension (see Hoeldtke, R. D., et al., Arch. Phys. Med. Rehabil., 69, 895–898, 1988 and Kooner, J. S., et al., Brit. J. Clin. Pharmacol., 28, 735P–736P, 1989); panic attacks (see Abelson, J. L., et al., Clin. Psychopharmacol., 10, 128–132, 1990); sclerodoma (see Soudah, H., et al., Clin. Res., Vol.39, p. 303A, 1991); small bowel obstruction (see Nott, D. M., et al., Brit. J. Surg., Vol. 77, p. A691, 1990); gastroesophageal reflux (see Branch, M. S., et al., Gastroenterology, Vol. 100, No. 5, Part 2 Suppl., p. A425, 1991); duodenogastric reflux (see Hasler, W., et al., Gastroenterology, Vol. 100, No.5, Part 2, Suppl., p. A448, 1991); Graves' Disease (see Chang, T. C., et al., Brit. Med. J., 304, p. 158, 1992); polycystic ovary disease (see Prelevic, G. M., et al., Metabolism Clinical and Experimental, 41, Suppl. 2, pp 76–79, 1992); upper gastrointestinal bleeding (see Jenkins, S. A., et al., Gut., 33, pp. 404–407, 1992 and Arrigoni, A., et al., American Journal of Gastroenterology, 87, p. 1311, (abs. 275), 1992); pancreatic pseudocysts and ascites (see Hartley, J. E., et al., J. Roy. Soc. Med., 85, pp. 107–108, 1992); leukemia (see Santini, et al., 78, (Suppl. 1), p. 429A (Abs. 1708), 1991); meningioma (see Koper, J. W., et al., J. Clin. Endocr. Metab., 74, pp. 543–547, 1992); and cancer cachexia (see Bartlett, D. L., et al., Surg. Forum., 42, pp. 14–16, 1991).

Accordingly, the present invention includes within its scope pharmaceutical compositions comprising, as an active ingredient, at least one of the peptides of formula (I) in association with a pharmaceutically acceptable carrier.

In general an effective dosage for the activities of this invention, for example the treatment of acromegaly, is in the range of 0.01 to 200 mg/kg/day, preferably 0.5 to 100mg/kg/day.

A peptide of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221, teaches polymeric sustained release compositions comprising a bioactive agent and chitosan. U.S. Pat. No. 5,916,883, issued Jun. 26, 1999, teaches sustained release compositions comprising a bioactive agent and cyclodextrin. International patent publication WO 99/38536 published Aug. 5, 1999, teaches absorbable sustained release compositions of a bioactive agent. U.S. Pat. No. 6,270,700, teaches a process for making microparticles comprising a therapeutic agent such as a peptide in an oil-in-water process. International patent publication WO 00/09166, published Feb. 24, 2000, teaches complexes comprising a therapeutic agent such as a peptide and a phosphorylated polymer. International patent publication WO 00/25826 published May 11, 2000, teaches complexes comprising a therapeutic agent such as a peptide and a polymer bearing a non-polymerizable lactone. The teachings of the foregoing patents and applications are incorporated herein by reference.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range is 0.01 to 5.0 mg/kg of body weight daily which can be administered as a single dose or divided into multiple doses.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

What is claimed is:

1. A method of eliciting a somatostatin agonist response in a human or other animal in need thereof, which comprises administering an effective amount of a peptide of formula (I)

$$X\text{-}A^1\text{-cyclo}(D\text{-Cys-}A^3\text{-}A^4\text{-Lys-}A^6\text{-}A^7)\text{-}A^8\text{-}Y, \qquad (I)$$

or a pharmaceutically acceptable salt thereof,
wherein

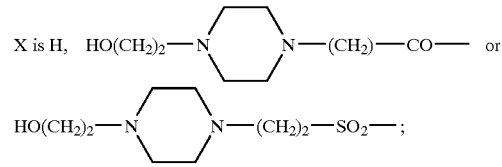

X is H, $HO(CH_2)_2-N\diagup\diagdown N-(CH_2)-CO-$ or $HO(CH_2)_2-N\diagup\diagdown N-(CH_2)_2-SO_2-$ ;

$A^1$ and $A^3$ are each independently the D- or L-isomer of an amino acid selected from the group consisting of Phe, Tyr, Tyr(I), Trp, 3-Pal, 4-Pal, Cpa and Nal;

$A^4$ is L-Trp, D-Trp, L-β-methyl-Trp or D-β-methyl-Trp;

$A^6$ is —NH—$(CHR^1)_n$—CO—, where n is 2, 3, or 4;

$A^7$ is L- or D-Cys;

$A^8$ is the D- or L-isomer of an amino acid selected from the group consisting of Phe, Tyr, Tyr(I), Trp, Nal, Cpa, Val, Leu, Ile, Ser and Thr;

Y is $NR^2R^3$ where $R^2$ and $R^3$ are each independently H or $(C_1-C_5)$alkyl;

$R^1$ is selected from the group consisting H, $(C_1-C_4)$alkyl and —$CH_2$-aryl; wherein said aryl is an optionally substituted moiety selected from the group consisting of phenyl, 1-naphthyl, and 2-naphthyl, wherein said optionally substituted moiety is optionally substituted with one or more substituents each independently selected from the group consisting of $(C_{1-6})$alkyl, $(C_{2-6})$alkenyl, $(C_{2-6})$alkynyl, aryl, aryl$(C_{1-6})$alkyl, $(C_{1-6})$alkoxy, —$N(R^4R^5)$, —COOH, —$CON(R^4R^5)$, halo, —OH, —CN, and —$NO_2$;

$R^4$ and $R^5$ each is, independently for each occurrence, H or $(C_{1-3})$alkyl;

where the Cys of $A^2$ is bonded to the Cys of $A^7$ by a di-sulfide bond formed from the thiol groups of each Cys, to the human or other animal.

2. A method of inhibiting the secretion of growth hormone, insulin, glucagon or pancreatic exocrine secretion in a human or other animal in need thereof, which comprises administering a peptide of formula (I)

$$X\text{-}A^1\text{-cyclo}(D\text{-Cys-}A^3\text{-}A^4\text{-Lys-}A^6\text{-}A^7)\text{-}A^8\text{-}Y, \qquad (I)$$

or a pharmaceutically acceptable salt thereof, wherein

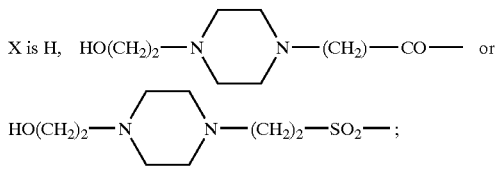

X is H, HO(CH$_2$)$_2$—N⟨⟩N—(CH$_2$)—CO— or

HO(CH$_2$)$_2$—N⟨⟩N—(CH$_2$)$_2$—SO$_2$—;

A$^1$ and A$^3$ are each independently the D- or L-isomer of an amino acid selected from the group consisting of Phe, Tyr, Tyr(I), Trp, 3-Pal, 4-Pal, Cpa and Nal;

A$^4$ is L-Trp, D-Trp, L-β-methyl-Trp or D-β-methyl-Trp;

A$^6$ is —NH—(CHR$^1$)$_n$—CO—, where n is 2, 3, or 4;

A$^7$ is L- or D-Cys;

A$^8$ is the D- or L-isomer of an amino acid selected from the group consisting of Phe, Tyr, Tyr(I), Trp, Nal, Cpa, Val, Leu, Ile, Ser and Thr;

Y is NR$^2$R$^3$ where R$^2$ and R$^3$ are each independently H or (C$_1$–C$_5$)alkyl;

R$^1$ is selected from the group consisting H, (C$_1$–C$_4$)alkyl and —CH$_2$-aryl; wherein said aryl is an optionally substituted moiety selected from the group consisting of phenyl, 1-naphthyl, and 2-naphthyl, wherein said optionally substituted moiety is optionally substituted with one or more substituents each independently selected from the group consisting of (C$_{1-6}$)alkyl, (C$_{2-6}$)alkenyl, (C$_{2-6}$)alkynyl, aryl, aryl(C$_{1-6}$)alkyl, (C$_{1-6}$)alkoxy, —N(R$^4$R$^5$), —COOH, —CON(R$^4$R$^5$), halo, —OH, —CN, and —NO$_2$;

R$^4$ and R$^5$ each is, independently for each occurrence, H or (C$_{1-3}$)alkyl;

where the Cys of A$^2$ is bonded to the Cys of A$^7$ by a di-sulfide bond formed from the thiol groups of each Cys, to said human or other animal.

3. The method according to claim 1 or 2, wherein said peptide of formula (I) is a peptide wherein A$^1$ is L-Phe, D-Phe, L-Cpa or D-Cpa;

A$^3$ is L-Tyr, L-Trp or L-3-Pal;

A$^4$ is D-Trp;

A$^6$ is β-Ala or Gaba;

A$^7$ is L-Cys;

A$^8$ is L-Thr, L-Trp, L-Leu or L-Nal; and

R$^2$ and R$^3$ are each H;

or a pharmaceutically acceptable salt thereof.

4. The method according to claim 1 or 2, wherein said peptide is of the formula Cpa-cyclo(D-Cys-3-Pal-D-Trp-Lys-Gaba-Cys)-Nal-NH$_2$;

Cpa-cyclo(D-Cys-3-Pal-D-Trp-Lys-β-Ala-Cys)-Nal-NH$_2$;

Phe-cyclo(D-Cys-3-Pal-D-Trp-Lys-Gaba-Cys)-Nal-NH$_2$;

Phe-cyclo(D-Cys-Tyr-D-Trp-Lys-Gaba-Cys)-Nal-NH$_2$;

Phe-cyclo(D-Cys-Trp-D-Trp-Lys-Gaba-Cys)-Nal-NH$_2$;

Phe-cyclo(D-Cys-Tyr-D-Trp-Lys-Gaba-Cys)-Trp-NH$_2$;

D-Phe-cyclo(D-Cys-Tyr-D-Trp-Lys-Gaba-Cys)Nal-NH$_2$;

D-Phe-cyclo(D-Cys-Tyr-D-Trp-Lys-Gaba-Cys)-Leu-NH$_2$; or

Phe-cyclo-(D-Cys-Tyr-D-Trp-Lys-Gaba-Cys)-Thr-NH$_2$;

or a pharmaceutically acceptable salt thereof.

5. The method according to claim 1 or 2, wherein said peptide is of the formula Cpa-cyclo(D-Cys-3-Pal-D-Trp-Lys-Gaba-Cys)-Nal-NH$_2$; or Cpa-cyclo(D-Cys-3-Pal-D-Trp-Lys-β-Ala-Cys)-Nal-NH$_2$;

or a pharmaceutically acceptable salt thereof.

6. The method according to claim 1 or 2, wherein said peptide or pharmaceutically acceptable salt thereof is in the form of a pharmaceutical composition which comprises an effective amount of a peptide of formula (I) or a pharmaceutically acceptable salt thereof, and a pharmaceutically acceptable carrier.

* * * * *